United States Patent [19]
Boebel et al.

[11] Patent Number: 5,290,287
[45] Date of Patent: Mar. 1, 1994

[54] ENDOSCOPIC COAGULATION FORCEPS

[75] Inventors: Manfred Boebel, Oetisheim; Siegfried Hiltebrandt, Knittlingen, both of Fed. Rep. of Germany

[73] Assignee: Richard Wolf GmbH, Knittlingen, Fed. Rep. of Germany

[21] Appl. No.: 943,955

[22] Filed: Sep. 11, 1992

[30] Foreign Application Priority Data

Nov. 9, 1991 [DE] Fed. Rep. of Germany ....... 4130064

[51] Int. Cl.⁵ .............................................. A61B 17/39
[52] U.S. Cl. .................................................... 606/51
[58] Field of Search ........................ 606/48, 50, 51, 52

[56] References Cited

U.S. PATENT DOCUMENTS 2,032,860  3/1936  Wappler et al.

FOREIGN PATENT DOCUMENTS

| 0210125 | 1/1987 | European Pat. Off. |
| 2325626 | 11/1974 | Fed. Rep. of Germany |
| 2415263 | 10/1975 | Fed. Rep. of Germany |
| 7518245 | 10/1975 | Fed. Rep. of Germany |
| 4032471 | 4/1992 | Fed. Rep. of Germany |
| 2161082 | 1/1986 | United Kingdom |

*Primary Examiner*—Lee S. Cohen
*Attorney, Agent, or Firm*—Panitch, Schwarze, Jacobs & Nadel

[57] ABSTRACT

Bipolar forceps for grasping and coagulating tissue, are constructed so as not to damage the mesosalpinx fused with a fallopian tube, when carrying out uterine tube sterilisation by coagulation. To this end the forceps are provided with a first and a second jaw for gripping and holding the tissue to be coagulated, the first jaw having a recess at its distal end and a mandrel being provided on the second jaw, which mandrel protrudes into the recess in the first jaw with clearance, when the jaws are in a closed position. A region between the jaws, which accommodates the tissue to be coagulated is limited distally by the mandrel and proximally by a limb of a bar on the first jaw for engaging in the second jaw when the jaws are in their closed position.

5 Claims, 2 Drawing Sheets

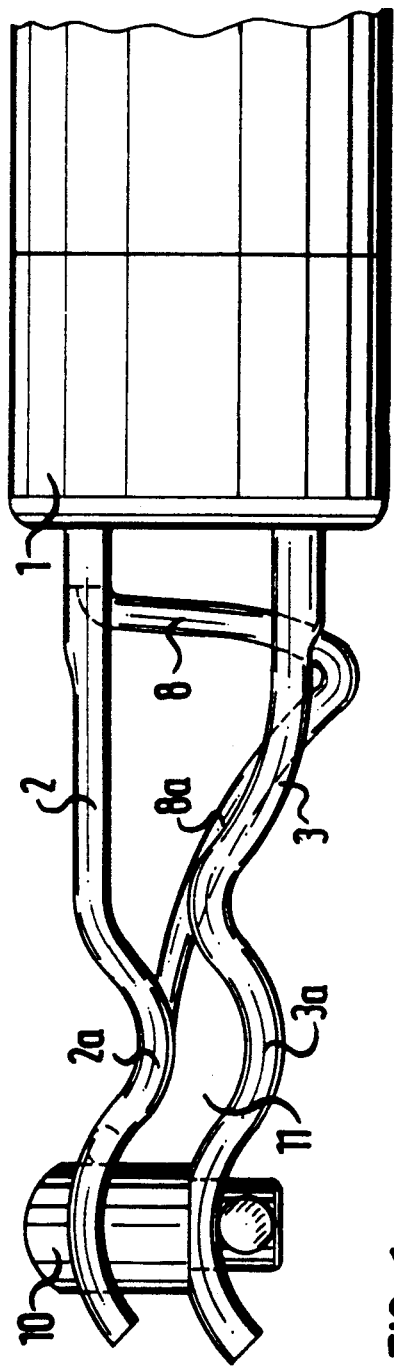
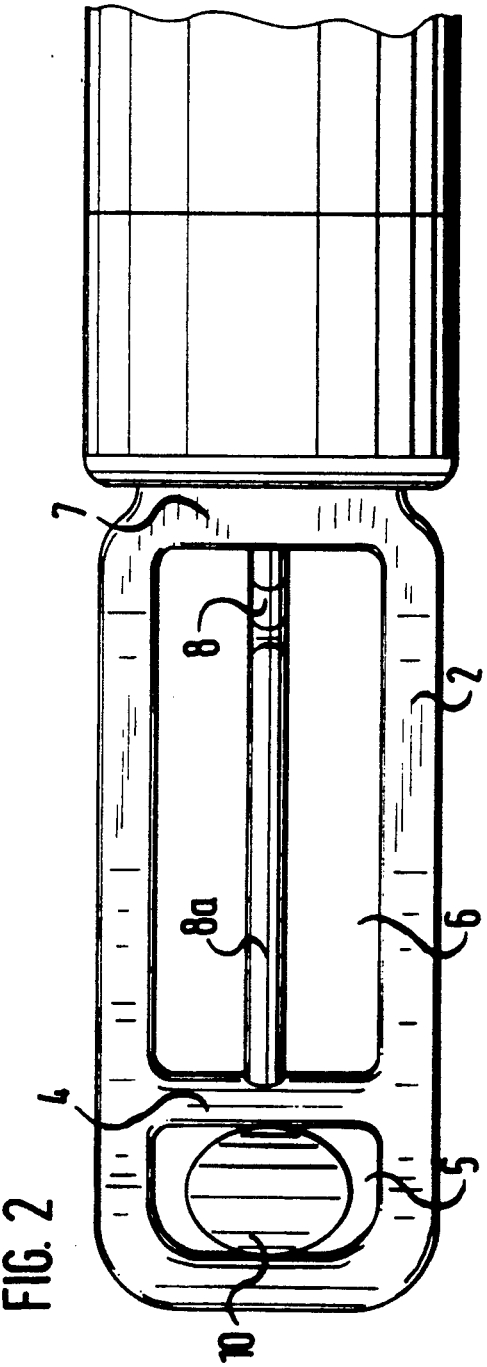

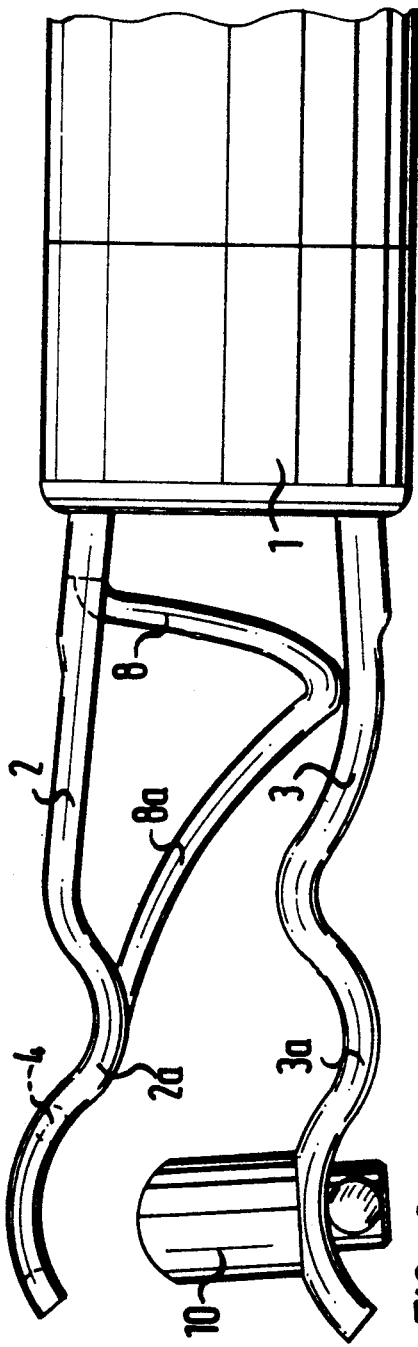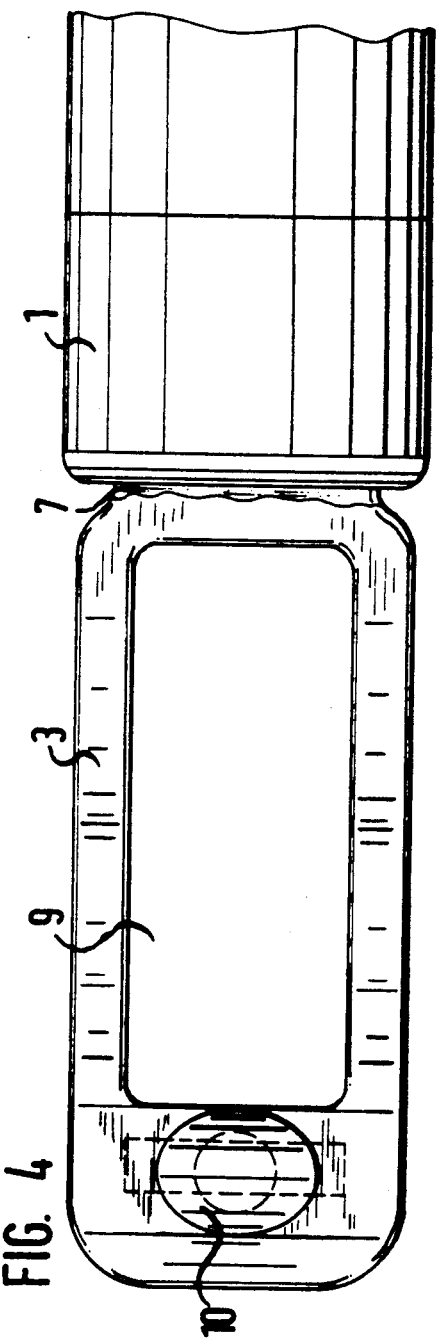

ENDOSCOPIC COAGULATION FORCEPS

FIELD OF THE INVENTION

This invention relates to bipolar forceps for grasping and coagulating tissue and comprising first and second jaws constituting electrodes, at the distal end of the forceps, for gripping and holding tissue to be coagulated, one of the jaws having a bar, for engaging in, and optionally through, the other jaw when the jaws are in a closed position.

BACKGROUND OF THE INVENTION

Coagulation forceps type are, for example, disclosed in German Utility Model No. 75 18 245. These forceps are especially intended for uterine tube sterilisation by coagulation of the fallopian tube and are provided to this end with jaws which are adapted to the fallopian tube to be coagulated. The distal part of one of the jaws is accordingly bent in the form of a hook so that the fallopian tube and the mesosalpinx can be pulled into the abdominal cavity for the appropriate treatment. Such displacement of the fallopian tube and the mesosalpinx has the advantage that coagulation can take place at a safe distance from the surrounding tissue of the body, so that damage to that tissue is avoided. The embodiment described ensures that the mesosalpinx is securely held not only above the fallopian tube, but also directly by means of the bent part of said one jaw.

Forceps for the electro-coagulation of anatomical structures by means of high-frequency current are also described in German Patent Application No. 2 325 626. These forceps have two pairs of mutually electrically insulated clamping jaws, having free end portions formed as hooks and which can be moved with respect to one another.

When carrying out uterine tube sterilisation by means of coagulation, it is important to avoid, inter alia, damaging the mesosalpinx during coagulation, thereby to avoid or exclude complaints and risks associated with the bleeding and/or scarring of the mesosalpinx.

SUMMARY OF THE INVENTION

According to the present invention one of the jaws has a recess at its distal end, a mandrel, which penetrates the recess with clearance when the jaws are in their closed position, being provided on the second jaw. A region between the jaws, for accommodating the tissue to be coagulated is limited distally by the mandrel and proximally by a limb of said engaging bar.

The mesosalpinx can thereby be positively gripped without damage thereto and independently of the fallopian tube using its elasticity, and outside the coagulating region, and can thus be drawn into the abdominal cavity while relieving the fallopian tube and can be securely held by means of the forceps.

Improved field distribution of the HF current and at the same time favourable positioning of tube-like tissue structures, such as fallopian tubes, in the coagulating region of the coagulation forceps, can be achieved if one end portion of said engaging bar, which portion is curved in the manner of a hook is connected to a first transverse bar proximally delimiting the recess at the distal end of the first jaw, the other end of said engaging bar being connected to a second transverse bar of the first jaw, opposite to the first transverse bar, said engaging bar bridging a further recess in the first jaw and extending in a plane which is perpendicular to that in which the tissue is gripped. Further, to these ends, the jaws may be of undulating shape over part of their length.

The curved portion of said engaging bar may have an apex which engages in a longitudinal recess in the second jaw when the jaws are in their closed position, the limb of said engaging bar extending as an arc from said apex to the first transverse bar. The gripped tissue is thereby securely fixed transversely of the length of the jaws of the coagulation forceps.

The mandrel, which is attached to the second jaw, may have a part upstanding therefrom, which is of atraumatic design at its free end and consists of PTFE, to ensure that the mandrel does not interfere with the HF field.

BRIEF DESCRIPTION OF THE DRAWINGS

FIG. 1 is a side view of coagulation forceps according to the preferred embodiment of the invention, when in a closed position;

FIG. 2 is a top plan view of the forceps as shown in FIG. 1;

FIG. 3 is a side view of the forceps when in an open position;

FIG. 4 is an under plan view of the forceps as shown in FIG. 1.

DETAILED DESCRIPTION OF THE PREFERRED EMBODIMENT OF THE INVENTION

Forceps for grasping and coagulating tissue comprise a mouth having a first and second jaws 2 and 3, respectively, and an instrument shaft 1 from which the jaws 2 and 3 project distally. The jaws 2 and 3 are pretensioned so as to be opened by spring force and can be actuated by axial displacement in the instrument shaft 1. That is to say the jaws 2 and 3 can be opened by pushing them outwards of the shaft 1 and can be closed by withdrawing them inwards of the shaft 1. The first jaw 2 comprises a frame of substantially rectangular shape, as seen in plan view (FIG. 2), defining a recess which is divided by means of a first cross bar 4 into a distally located first recess 5 extending transversely of the longitudinal axis of the instrument and being of substantially oval shape, and a proximally located second recess 6 extending axially of the instrument and being of substantially rectangular shape as seen in plan view. The second recess 6 is delimited proximally by a second cross bar 7. As seen in top plan view in FIG. 2, the second recess 6 is divided symmetrically by a bar 8 extending axially of the instrument and which is firmly anchored at its distal end to the first cross bar 4 and at its proximal end to the second cross bar 7. As shown in FIGS. 1 and 3, the bar 8 has a hook-like lower curved portion which engages in a recess 9 in the second jaw 3. The recess 9 is substantially aligned with the second recess 6 in the first jaw 2 when the jaws 2 and 3 are in their closed position. The second jaw 3 is provided proximate to its distal end with a mandrel 10 made of polytetrafluoroethylene (PTFE). The mandrel 10 upstands from the jaw 3. The upstanding part of the mandrel 10 is shaped so as to be atraumatic. When the jaws 2 and 3 are in their closed position, the mandrel 10 protrudes as shown in FIG. 1 into the first recess 5 of the first jaw 2 with slight clearance. Both of the jaws 2 and 3 have an undulating shape as shown in FIGS. 1 and 3, so that in their closed position (FIG. 1) the jaws 2 and 3 cooperate to define an arcuate, contracted, laterally open region 11 delimited by equidistant portions 2a and 3a of the jaws 2 and 3 just proximally of the mandrel 10. The tissue to be coagulated is accommodated in the region 11 which is limited distally by the mandrel 10 and proximally by a limb 8a of the bar 8. The bar 8 extends in the direction of relative movement of the jaws 2 and 3, that is to say in a plane which is perpendicular to that in which the tissue is gripped.

In use, the coagulation forceps are introduced into the body cavity conventionally, by means of a trocar sleeve in which the jaws 2 and 3 are held in their closed position. After being introduced into the body cavity, the jaws 2 and 3 are opened so that the fallopian tube to be coagulated is received between the jaws 2 and 3 until the fallopian tube comes to rest against the proximal side of the mandrel 10 and in the region 11 between the jaws 2 and 3. The mesosalpinx is situated in the region of the mandrel 10 in this position. As the jaws 2 and 3 approach one another as they are being closed, the mesosalpinx is initially turned into the first recess 5 in the manner of a push button, damaging shearing of the mesosalpinx being avoided by virtue of the clearance between the edge of the recess 5 and the mandrel 10. Simultaneously the fallopian tube increasingly expands over the entire region 11, which is delimited by the limb 8a of the bar 8 protruding into the recess 9 and by the mandrel 10.

In order to close off the fallopian tube by coagulation the entire tissue structure can be drawn by appropriate displacement of the instrument into the abdominal cavity without the risk of damage to the mesosalpinx, by virtue of the positive fixation of the mesosalpinx and the fallopian tube, so that coagulation can be carried out in the abdominal cavity without endangering the surrounding tissue. Coagulation is then concentrated in the region 11 between jaws 2 and 3.

What is claimed is:

1. Bipolar forceps for grasping and coagulating tissue, the forceps having a proximal end and a distal end and comprising first and second jaws having at said distal end electrodes for gripping and holding tissue to be coagulated, the jaws being relatively movable between an open position and a closed tissue gripping position, the second jaw having a recess, the first jaw having an engaging bar extending toward and aligning with the recess of the second jaw, the recess permitting the engaging bar to engage the second jaw when the jaws are in their closed position, the first jaw having a distal recess and the second jaw having a mandrel extending toward and aligning with the distal recess of the first jaw, said distal recess permitting the mandrel to protrude therethrough and to engage the first jaw when the jaws are in their closed position, the jaws cooperating to define a region for receiving the tissue to be coagulated, said region being delimited distally by said mandrel and proximally by said bar.

2. Forceps as claimed in claim 1, wherein the engaging bar has first and second ends and an extending curved portion disposed therebetween and wherein the first jaw further comprises first and second transversely positioned bars, the first transverse bar proximally delimiting the distal recess of the first jaw and distally delimiting a proximal recess of the first jaw, and the second transverse bar proximally delimiting the proximal recess, the engaging bar bridging the proximal recess and being connected at the first en to the first transverse bar and at the second end to the second transverse bar.

3. Forceps as claimed in claim 2, wherein said recess in the second jaw is a longitudinal recess and wherein said curved portion of said engaging bar comprises an apex which engages said longitudinal recess of the second jaw when said jaws are in their closed position, said curved portion of said engaging bar comprising a generally arc-shaped extension connecting said apex to said first transverse bar.

4. Forceps as claimed in claim 1, wherein said jaws have a generally undulating shape over a part of their respective lengths.

5. Forceps as claimed in claim 1, wherein said mandrel has a free end which is of a generally curved shape, so as not to cause trauma to tissue, and comprises polytetrafluoroethylene.

* * * * *

UNITED STATES PATENT AND TRADEMARK OFFICE
CERTIFICATE OF CORRECTION

PATENT NO. : 5,290,287
DATED : March 1, 1994
INVENTOR(S) : Manfred Boebel et al.

It is certified that error appears in the above-indentified patent and that said Letters Patent is hereby corrected as shown below:

On the title page,

In the left-hand column, under [30], replace "Nov. 9, 1991" with --Sept. 11, 1991--.

Signed and Sealed this

Twenty-eight Day of February, 1995

Attest:

BRUCE LEHMAN

*Attesting Officer*    *Commissioner of Patents and Trademarks*